(12) United States Patent
Dandl et al.

(10) Patent No.: US 10,314,801 B2
(45) Date of Patent: Jun. 11, 2019

(54) TASTE-MASKED ORAL PHARMACEUTICAL COMPOSITION

(71) Applicant: HERMES ARZNEIMITTEL GMBH, Pullach (DE)

(72) Inventors: Klaus Dandl, Oberhaching (DE); Detlev Haack, Pullach (DE); Karin Becker, Gröbenzell (DE); Andreas Zimmer, Graz (AT); Claudia Lang, Pullach (DE); Sharareh Salar Behzadi, Vienna (AT)

(73) Assignee: HERMES ARZNEIMITTEL GMBH, Pullach (DE)

( * ) Notice: Subject to any disclaimer, the term of this patent is extended or adjusted under 35 U.S.C. 154(b) by 0 days.

(21) Appl. No.: 15/320,272

(22) PCT Filed: Jun. 19, 2015

(86) PCT No.: PCT/EP2015/063841
§ 371 (c)(1),
(2) Date: Dec. 19, 2016

(87) PCT Pub. No.: WO2015/193485
PCT Pub. Date: Dec. 23, 2015

(65) Prior Publication Data
US 2017/0157049 A1 Jun. 8, 2017

(30) Foreign Application Priority Data
Jun. 20, 2014 (EP) .................................. 14173273

(51) Int. Cl.
| A61K 9/00 | (2006.01) |
| A61K 9/50 | (2006.01) |
| A61K 33/06 | (2006.01) |
| A61K 31/167 | (2006.01) |
| A61K 31/192 | (2006.01) |
| A61K 31/522 | (2006.01) |

(52) U.S. Cl.
CPC .......... *A61K 31/192* (2013.01); *A61K 9/0056* (2013.01); *A61K 9/5015* (2013.01); *A61K 9/5089* (2013.01); *A61K 31/167* (2013.01); *A61K 31/522* (2013.01); *A61K 33/06* (2013.01)

(58) Field of Classification Search
None
See application file for complete search history.

(56) References Cited

U.S. PATENT DOCUMENTS

| 4,687,662 A | 8/1987 | Schobel et al. |
| 5,180,590 A * | 1/1993 | Carcano ............... A61K 9/0007 424/466 |
| 5,445,827 A | 8/1995 | Fritsch et al. |
| 5,587,179 A | 12/1996 | Gergely et al. |
| 5,728,403 A * | 3/1998 | Mauger ................ A61K 9/1617 424/469 |
| 5,891,476 A | 4/1999 | Reo et al. |
| 6,274,172 B1 | 8/2001 | Mention et al. |
| 7,569,274 B2 | 8/2009 | Besse et al. |
| 8,147,874 B2 | 3/2010 | Ziegler et al. |
| 9,636,307 B2 * | 5/2017 | Becker ................. A61K 9/5015 |
| 2003/0180352 A1 * | 9/2003 | Patel .................... A61K 9/1617 424/465 |
| 2005/0003015 A1 * | 1/2005 | Sakai ................... A61K 9/0095 424/489 |
| 2006/0034937 A1 | 2/2006 | Patel et al. |
| 2010/0092569 A1 | 4/2010 | Lorenzon et al. |
| 2011/0212171 A1 * | 9/2011 | Venkatesh ............ A61K 9/0056 424/464 |
| 2011/0237616 A1 | 9/2011 | Dungan et al. |
| 2011/0250244 A1 * | 10/2011 | Kraahs .................. A61K 9/501 424/400 |
| 2015/0366823 A1 | 12/2015 | Dandl et al. |

FOREIGN PATENT DOCUMENTS

| EP | 0839528 | 5/1998 |
| JP | 2007051133 | 3/2007 |
| JP | 2008007496 | 1/2008 |
| WO | WO 2008/071407 | 6/2008 |
| WO | WO 2009/130204 | 10/2009 |
| WO | WO 2010/037543 | 4/2010 |
| WO | WO 2010/070028 A1 | 6/2010 |

(Continued)

OTHER PUBLICATIONS

S Fulzele, S Rieschl. "Taste-Masking—Pharmaceutical Taste-Masking Technologies." Drug Development and Delivery, Jul./Aug. 2015, 5 printed pages. http://www.drug-dev.com/Main/Back-Issues/TASTEMASKING-Pharmaceutical-TasteMasking-Technolog-962.aspx, accessed Dec. 12, 2017. (Year: 2015).*

"Acetaminophen USP/Paracetamol Ph Eur Special Granular", Aug. 1, 2010, 1 page.

Sheskey et al., "Palm Oil, Hydrogenated: Pharmaceutical Excipients", Handbook of Pharmaceutical Excipients, Medicines Complete, May 1, 2014, 2 pages.

Sinchaipanid, et al., "Application of hot-melt coating for controlled release of propranolol hydrochloride pellets", Powder Technology, 2004, 141:203-209.

International Search Report for International Application No. PCT/EP2015/063841, prepared by the International Search Authority, dated Aug. 31, 2015.

Griffin, "Calculation of HLB Values of Non-Ionic Surfactants," Journal of the Society of Cosmetic Chemists, 5(4): 249-256 (1954).

Hatton et al., "Efficacy and Safety of Oral Phenylephrine: Systematic Review and Meta-Analysis," The Annals of Pharmacotherapy, 41(3): 381-390 (2007).

(Continued)

*Primary Examiner* — Isaac Shomer
(74) *Attorney, Agent, or Firm* — Hoxie & Associates LLC

(57) ABSTRACT

The invention provides coated particles with a taste-masked drug substance. The particles comprise a core with the agglomerated active ingredient and a coating comprising a triglyceride and a surfactant. The particles exhibit rapid drug release and a stable release profile. Moreover, the invention provides a hot-melt coating method for manufacturing such particles, and pharmaceutical compositions comprising the particles. The method allows the coating of core particles at moderate temperatures, thereby preventing the degradation of the thermolabile active ingredient.

19 Claims, No Drawings

(56) References Cited

FOREIGN PATENT DOCUMENTS

| WO | WO 2013/049365 | 4/2013 | |
| WO | WO-2014167124 A1 * | 10/2014 | ........... A61K 9/5015 |

OTHER PUBLICATIONS

International Search Report for International Application No. PCT/EP2014/052286, prepared by the International Search Authority, dated Jul. 7, 2014, 5 pages.

International Search Report for International Application No. PCT/EP2014/057442, prepared by the International Search Authority, dated May 22, 2014, 3 pages.

IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. https://doi.org/10.1351/goldbook.

JP 2007051133, Rohto Pharma, "Tablet Composition," Mar. 1, 2007, English language machine translation of abstract, Espacenet, date obtained: Nov. 28, 2017, 1 page, <URL: https://worldwide.espacenet.com/publicationDetails/biblio?CC=JP&NR=2007051133A&KC=A&FT=D&ND=3&date=20070301&DB=&locale=en_EP>.

JP 2008007496, Zenyaku Kogyo KK, "Method for Producing Preparation Using Stirring Type Granulator," Jan. 17, 2008, English language machine translation of abstract, Espacenet, date obtained: Nov. 28, 2017, 1 page, <URL: https://worldwide.espacenet.com/publicationDetails/biblio?II=0&ND=3&adjacent=true&locale=en_EP&FT=D&date=20080117&CC=JP&NR=2008007496A&KC=A>.

WO 2008/071407, Grunenthal GMBH, "Coated Pellets," Jun. 19, 2008, English language machine translation of abstract, Espacenet, date obtained: Nov. 28, 2017, 1 page, <URL: https://worldwide.espacenet.com/publicationDetails/biblio?CC=WO&NR=2008071407A2&KC=A2&FT=D&ND=3&date=20080619&DB=&locale=en_EP>.

Anonymous, "Nonionics-Esters," Surfactants Europe: A directory of surface active agents available in Europe, p. 290, Jan. 1, 1995, Retrieved on May 29, 2018, ISBN: 978-0-85404-804-5

Anonymous, "Room Temperature," Wikipedia, pp. 1-3, Apr. 22, 2018, Retrieved from the Internet on May 29, 2018, URL: <https://en.wikipedia.org/wiki/Room_temperature>.

* cited by examiner

TASTE-MASKED ORAL PHARMACEUTICAL COMPOSITION

CROSS REFERENCE TO RELATED APPLICATIONS

This application is a United States Application under 35 U.S.C. § 371 claiming benefit of PCT Application No. PCT/EP2015/063841, filed on Jun. 19, 2015, which claims the benefit of European Patent Application No. 14173273.5, filed on Jun. 20, 2014, the contents of each of which are incorporated herein by reference in their entireties.

FIELD OF THE INVENTION

The present invention relates to the field of pharmaceutics, and concerns oral drug formulations, their manufacture and their use.

BACKGROUND OF THE INVENTION

Most patients prefer to take orally administered medicaments over other routes of administration. However, in order to be acceptable to patients, an oral drug product must be easily swallowed and without unpleasant or bitter taste or other undesirable organoleptic properties.

Many drug substances, also commonly referred to as active pharmaceutical ingredients (API), exhibit a rather poor taste. A poor taste often means a significant level of bitterness, but may also involve other unpleasant sensations such as a burning, stinging, metallic, or astringent mouthfeel.

While taste masking is generally rather easy to achieve with a conventional tablet which may be coated with a suitable polymeric coating, and also in the case of a capsule formulation wherein the capsule shell itself provides a barrier which prevents contact between the active ingredient and the oral mucosa of the patient during administration, it is much more challenging to mask the taste of a compound having a poor taste when formulated as a dispersible, effervescent, or orally disintegrating dosage form or as granules for direct oral administration ("direct-to-mouth granules"), because in these cases the dosage unit is not swallowed as a whole, but the formulation comes into substantial contact with the oral mucosa. In the case of effervescent formulations, the drug typically dissolves in a larger amount of water, such as 200 mL, and in this diluted form, sufficient taste masking may be achieved through the incorporation of sweetening agents and flavours. Most challenging in terms of taste is the formulation of the active ingredient in dosage forms whose administration potentially allows the drug to contact the oral mucosa in concentrated form, as in the case of orally disintegrating tablets or granules for direct oral administration. On the other hand, such dosage form designs are highly desirable for high-dose drugs because of their excellent swallowability even without water.

Further technical challenges arise when the API is not easily processable, for example due to sensitivity to thermal stress or moisture. Another particular difficulty is the processing of mechanically unstable API particles, especially of drug particles which represent agglomerates or granules. Poor mechanical stability of the API particles means that they cannot easily be coated as the heat and mechanical stress involved in most coating processes would lead to the diminution or disintegration of the agglomerate, which would cause the generation of undesirable API dust and a substantially reduced coating efficiency. In result, the taste-masking effect would not be sufficient, at least not if the API is to be incorporated within an oral (direct-to-mouth) granule formulation or an orally disintegrating tablet.

Nevertheless, effective taste-masking may require that a coating is provided on the surface of the active ingredient. The coating serves as a physical barrier layer between the active ingredient and the patient's taste buds and olfactory receptors. In addition, a coating may be useful also to protect a sensitive or labile active ingredient during storage.

In principle, taste-masking coatings may be polymeric film coatings or lipidic coatings. Polymeric coating systems are sprayed onto drug cores as aqueous or organic solutions or dispersions. A disadvantage of organic solvents is their need for special equipment and their negative impact on the environment. Aqueous coating systems also consume substantial energy, as the polymeric coating material must be heated above its film-forming temperature in order to coalesce, and the removal of water require more extensive drying than that of typical organic solvents. Moreover, many polymeric coating systems show curing effects, i.e. their properties change over time, so that the drug dissolution behaviour may become compromised during storage.

In principle, a lipid coating may be applied to API particles by various thermal processing methods such as melt extrusion, spray congealing, melt coating in a mixer, fluid-bed coating, and the like.

Lipidic coating systems, such as coatings based on waxes like carnauba wax, do not require a solvent to be applied to drug-containing cores: They may often be used as melts in hot-melt coating processes. On the other hand, these types of coatings, due to the poor water solubility of its main constituents, also tend to have substantial negative impact on the drug's release profile, especially if rapid drug release is required. For example, Sinchaipanid et al (Powder Technology, 2004, 141, 203-209) describe the hot-melt coating of granulated propranolol hydrochloride pellets using a coating consisting of a mixture of Precirol® ATO5, (glyceryl palmitostearate, which comprises primarily diglycerides of palmitic and stearic acid) and Gelucire® 50/02 (saturated polyglycolysed glycerides). Compared to uncoated propranolol pellets, addition of the coating resulted in a significant decrease in drug release rate—in fact providing for regulated and controlled release of the drug. In cases where immediate release of a drug is required wax coatings are thus often not successful.

The stability of a lipidic or waxy taste-masking coating itself over time can also impact the release profile of the active ingredient. The conversion of an initially formed polymorph of a coating excipient to a thermodynamically more stable crystal form over time during the course of storage, sometimes also triggered by an exposure to different environmental conditions, can lead to significant and undesirable variations in the drug dissolution profile of the composition.

Furthermore, the hot-melt processing conditions may be critical to temperature-sensitive drug compounds. Depending on the type of lipidic or waxy coating material, the coating process are sometimes conducted at temperatures of higher than 60° C., and sometimes also higher than 80° C. or even 100° C. Depending on the type of equipment that is used, additional disadvantages such as high shear or pressure may make the coating process unattractive for certain APIs, in particular mechanically unstable API particles such as agglomerates.

WO 2010/037543 A1 describes the extrusion of lipid pellets for taste masking. The method requires the mixing of the active ingredient with a lipid mixture comprising a hard fat and glycerol trimyristate or glycerol distearate, followed by cold extruding the mixture and spheronising the extrudate to obtain pellets or spherical granules. Provided that a sufficient amount of lipid material is used, a coating is formed which completely covers the surface of the pellets and which preferably has a thickness of at least 5 nm. A major disadvantage is however that the release of the incorporated drug substance is substantially decelerated, even in the case of a readily water-soluble compound such as sodium benzoate. The inventor reports that even after 45 min of dissolution testing at 37° C., the drug is not completely released from the formulation.

WO 2008/071407 A2 discloses immediate or rapid release pellets comprising cefpodoxim, an antibiotic compound having a poor taste. The pellets exhibit a taste-masking coating comprising carnauba wax and a hydrogel former such as a cellulose polymer derivative, alginate or gum. It is mentioned in the document that many lipophilic substances, such as cocoa butter or Precirol®, are prone to polymorphic changes during storage. As the structural changes would lead to inconsistencies in the dissolution profiles, such compounds are deemed to be unsuitable for use as coating excipients for these pellets. The document therefore teaches the use of waxes such as carnauba wax which have a high melting range and which do not exhibit any polymorphic changes.

U.S. Pat. No. 5,891,476 discloses acetaminophen particles or granules coated with a non-polymorphic waxy component such as carnauba wax and optionally other lipid components and/or surfactants. According to the document, the use of such waxes removes the risk of variable dissolution rates resulting from changing morphology of the coating over time and under different conditions.

However, a disadvantage in using waxy components having a high melting point such as carnauba wax (melting range approx. 82 to 86° C.) in hot-melt coatings is that the active ingredient itself may also be subjected to the higher temperatures required to maintain the coating components in melt-phase during the coating process. Higher temperatures during processing can increase the degradation of thermolabile active ingredients. Moreover, hot-melt coating processes involving molten carnauba wax are very difficult to handle because the coating composition must be kept at even higher temperatures, e.g. at about 100° C. or higher, and since this wax solidifies very rapidly upon cooling down, it tends to clog the tubes through which it is pumped to the spray nozzle, as well as the nozzle itself.

WO 2010/070028 A1 discloses various taste-masked, hot-melt coated compositions incorporating the active ingredients acetaminophen, ranitidine, and caffeine. The coatings comprise, as a meltable lipophilic excipient, stearic acid, Precirol ATO 5 (a mixture of mono-, di- and triglycerides of palmitic and stearic acid), or Compritol 888 ATO (glyceryl behenate). The coatings further comprise a release compound, i.e. a compound which enhances the disintegration of the taste-masking layer in the gastrointestinal fluid, such as by the formation of pores or holes through swelling (e.g. Amberlite IRP 88) or carbon dioxide release (e.g. calcium carbonate); and a surfactant or other substance (e.g. PEG 3000 or Tween 20) which is incorporated to achieve a homogeneous distribution of the release compound in the meltable lipophilic excipient. However, the resulting coating compositions are rather complex. Due to the insolubility of the release compound in the meltable lipophilic compound, there is a risk of phase separation during the coating process, leading to poor reproducibility. Moreover, as the document is silent on this aspect, it is unclear whether the release profiles achieved with such complex and inherently incompatible coating compositions are stable under storage conditions.

US 2010/0092569 A1 relates to the taste-masking of conjugated linoleic acid compounds by suspending an adsorbate of the active ingredient on silica powder in a molten lipid matrix and subsequent spray cooling, such as to form coated particles. The lipid matrix comprises triglycerides of C16, C18, C20 and C22 saturated fatty acids and 3 wt.-% of an unidentified emulsifier whose function is to ensure a homogeneous dispersion of the active ingredient in the molten lipid. The purpose of the coating is to protect the light- and air-sensitive linoleic acid compound from degradation. The taste-masked product is used as an additive in animal feed.

However, the preparation of a melt suspension involves the full exposure of the active ingredient to temperatures higher than the melting range of the lipid, in the present case about 70° C., which may be acceptable in the case of some active ingredients or in the case of animal feeds, but not for temperature-sensitive pharmaceutical compounds for human use. Moreover, the document is silent as to the resulting dissolution profiles, which do not appear to have any relevance in this case.

It is an object of the invention to provide an improved method for the taste-masking of drug substances that are mechanically unstable, such as agglomerated API particles. Moreover, it is an object to provide an improved taste-masked form of agglomerated drug particles which are immediate release, i.e. which exhibits rapid drug dissolution and a stable dissolution profile. It is also an object to provide improved methods and compositions for the masking of the taste of agglomerated drug particles which are heat or moisture sensitive. A further object is to provide improved pharmaceutical compositions comprising taste-masked agglomerated drug particles with rapid drug dissolution. A yet further object is to provide taste-masked compositions which may be manufactured at moderate, as well as processes by which taste-masked compositions of sensitive compounds may be prepared. Moreover, it is an object to overcome one or more of the limitations or disadvantages associated with the prior art. Other objects will become clear on the basis of the description and the claims.

These and other objects are achieved by the subject-matter as defined in the independent claims below, with particular embodiments outlined in the dependent claims.

SUMMARY OF THE INVENTION

The invention provides, according to a first aspect, a coated particle which comprises a core and a coating. The core comprises an agglomerated active ingredient, and the coating comprises a triglyceride which is solid at room temperature and a surfactant. The coated particle allows for immediate release, i.e. rapid dissolution of the active ingredient in an aqueous medium.

The core may consist of an agglomerated particle, such as a granule or pellet, comprising the active ingredient and one or more pharmaceutical excipients. It preferably comprises at least about 10 wt.-% of active ingredient.

The solid triglyceride is preferably a saturated triglyceride. Its three fatty acid chains may be identical, as in trimyristin (or glyceryl trimyristate), tripalmitin (or glyceryl tripalmitate), tristearin (or glyceryl tristearate), triarachidin (or glyceryl triarachidate), or tribehenin (or glyceryl tribehenate). Tripalmitin and tristearin are among the preferred triglycerides.

The surfactant may be a non-ionic surfactant, such as a polysorbate. Polysorbate 65 is one of the preferred surfactants, in particular in combination with a saturated triglyceride selected from tripalmitin and tristearin. Optionally, the weight ratio of the triglyceride to the surfactant may be in the range from 70:30 to 90:10, in particular in the case of tripalmitin or tristearin and polysorbate 65. The coating may essentially consist of the triglyceride and the polysorbate.

In a further aspect, the invention provides a method for the preparation of coated particles comprising a core with an agglomerated active ingredient and a coating with a triglyceride which is solid at room temperature and a surfactant. The method includes the steps of (a) providing a core particle comprising an agglomerated active ingredient, (b) providing a coating composition comprising a molten triglyceride and a surfactant, and (c) coating the core particle with the coating composition. It is preferably carried out in a fluid-bed coater or in an air flow bed coater. The product temperature may be kept at about 20 to 50° C. during the coating step (c).

The invention may also relate to an immediate release particle comprising a core and a coating, wherein the core comprises an agglomerated active ingredient, and wherein the coating comprises a triglyceride which is solid at room temperature and a surfactant, said particle being obtainable by a method comprising the steps of (a) providing a core particle comprising an agglomerated active ingredient, (b) providing a coating composition comprising a molten triglyceride and a surfactant, and (c) coating the core particle with the coating composition.

In yet a further aspect, the invention provides a pharmaceutical composition comprising immediate-release coated particles comprising an agglomerated active ingredient core and a coating with a triglyceride which is solid at room temperature and a surfactant. The composition may optionally be formulated as granules, such as dispersible granules, effervescent granules, direct-to-mouth granules, or as a tablet, such as a dispersible tablet, an effervescent tablet, or an orally disintegrating tablet.

DETAILED DESCRIPTION OF THE INVENTION

In a first aspect, the invention provides a coated particle which comprises a core and a coating. The core comprises an agglomerated active ingredient, and the coating comprises a triglyceride which is solid at room temperature and a surfactant. The particles also allow for immediate release, or rapid dissolution, of the active ingredient in the presence of an aqueous medium. The amount of the agglomerated active ingredient is at least 10 wt.-%, relative to the weight of the core. According to the invention, the coated particle has a specific structure, comprising at least one core and at least one coating layer. The core comprises an agglomerated active ingredient, such as a granule or a pellet, which may in turn be composed of primary particles such as crystals. The coated particle is useful as a component of a pharmaceutical composition for oral use.

The core is typically solid, optionally semi-solid, and comprises an agglomerated pharmacologically active ingredient. The agglomerated active ingredient may be crystalline, non-crystalline or partially crystalline. The primary particles of the active ingredient are associated in the form of agglomerates such as pellets, micropellets, granules, or microparticles. The shape of the core, i.e. of the agglomerated active ingredient, primarily depends on the nature, composition and manufacturing method of the core material and/or agglomerate. As used herein, the terms "agglomerated", "agglomerate" or "agglomeration" includes materials prepared by wet or dry granulation, compaction such as roller compaction, pelletisation, slugging, and the like. A granulated active ingredient is also an agglomerated active ingredient. The particle size of the agglomerated active ingredient as determined by sieving (i.e. sieve diameter) is typically below about 2.5 mm, and preferably below about 1.5 mm. In further preferred embodiments, the core has a diameter in the range from about 100 to about 1,000 µm, from about 80 to about 600 µm, from about 100 to about 400 µm, or from about 300 to 800 µm, respectively. In some other preferred embodiments, the particle size of the core is from about 200 to 500 µm, or from about 250 to 750 µm.

Optionally, the core substantially consists of an agglomerated active ingredient. In this context, the term "substantially consists of" means that no further components have been added to the active ingredient in order to prepare the core and/or agglomerate. Nevertheless, very small amounts of other materials may be present, such as impurities.

Alternatively, the core may comprise an agglomerated active ingredient that is a composite agglomerated particle, or a formulated agglomerated particle that comprises an active ingredient and at least one pharmaceutically acceptable excipient. For example, a granule, pellet or micropellet comprising an active ingredient and at least one binder may be used. Commonly known methods for formulating and manufacturing such granules, pellets or micropellets may be used. In a particularly preferred embodiment, the core comprises an agglomerate of an active ingredient and a binder, such as microcrystalline cellulose.

The core comprises at least about 10 wt.-% of active ingredient. In further preferred embodiments, the core comprises at least about 30 wt.-% of active ingredient, or at least about 50 wt.-%, or at least about 60 wt.-%, or at least about 70 wt.-%, or at least about 80 wt.-%, or at least about 90 wt.-%, or at least about 95 wt.-%, or even at least about 98 wt.-% of active ingredient, respectively. It is understood that these percentages are relative to the weight of the core. Of course, the core (or even the coating) may further comprise some non-agglomerated active ingredient as long as the amount of agglomerated active ingredient in the core is at least 10 wt.-%.

In particular, the core may comprise agglomerates of an active ingredient with undesirable organoleptic properties such as bitterness, burning, stinging, metallic, or astringent mouthfeel when administered orally and which requires taste-masking. The active ingredient may, for example, be selected from analgesics, non-steroidal antiinflammatory drugs, proton pump inhibitors, cough suppressants, antihistamines, stimulants, sedatives, decongestants, antiemetics, phosphate-binding agents, and sympathomimetics.

Preferred active ingredients include ibuprofen, paracetamol, caffeine, calcium acetate, aspirin, pseudoephedrine, dimenhydrinate, omeprazole, pantoprazole, or lansoprazole, or any of their salts, isomers, polymorphs, and hydrates.

In one of the particularly preferred embodiments, the active ingredient is agglomerated ibuprofen, or an agglomerated ibuprofen salt, in particular agglomerated ibuprofen sodium or ibuprofen potassium. According to another preferred embodiment, the invention provides an immediate release particle comprising a core and a coating, wherein the core comprises agglomerated ibuprofen, ibuprofen potassium or ibuprofen sodium (e.g. dihydrate), and wherein the coating comprises a triglyceride which is solid at room temperature and a surfactant. The coating is understood as a layer, or several layers, of material substantially enclosing the core, or at least the majority of the core surface. As it is an important objective of the invention to provide effective taste-masking of the active ingredient, it is preferred that at least 80% of the surface, or at least 90% of the surface, or at least 95% of the surface, or substantially all of the surface of the core is covered by the coating. At the same time, it will be appreciated by a person skilled in pharmaceutics that a bulk material comprising multiple particles according to the invention may include a minor fraction of particles whose coatings may not completely or substantially cover the cores, even though the majority of the particles exhibit substantially complete coatings.

The coating of the invention comprises at least a triglyceride which is solid at room temperature and a surfactant. As used herein, a triglyceride is an ester derived from glycerol and three fatty acids. A triglyceride may also be referred to as a triacylglyceride, or a fat. The composition of the coating is of key importance to the invention.

Agglomerated particles often have uneven, irregular surfaces, which may also be porous. The efficient application of an effective layer of coating is therefore usually challenging. This has particular consequences for agglomerated particles comprising active ingredients which require taste-masking. It has been found that a coating composition comprising a triglyceride which is solid at room temperature and a surfactant is especially amenable towards the coating of agglomerated particles in terms of processing, as well as achieving good taste-masking and adequate drug release times. It has been found that such coating composition, when applied as a melt, readily covers the surface of the agglomerates and is particular effective in achieving taste masking.

Wax or lipid-based coatings typically provide taste-masking but also delay release of the active ingredient. In contrast, it has been found that the coated particles of the invention are taste-masked, but at the same time advantageously able to provide immediately release of the active ingredient. The particles are thus particularly suited for use in immediate-release pharmaceutical compositions. As defined herein, immediate release, or rapid dissolution, means a dissolution profile in which at least 75% of the active ingredient is dissolved in 45 minutes, as determined using a USP Dissolution Apparatus type 2 (paddle apparatus) in 900 mL of an aqueous medium at a pH value at which the active ingredient may be soluble and stable at 37° C., preferably 0.1 N hydrochloride acid, and at a stirring speed of 100 rpm. The term immediate release may be used synonymously with the terms fast release, rapid release, rapid dissolution, quick release, or the like, as opposed to modified, slow, extended, controlled, or sustained release.

In a particular embodiment of the invention, the coated particles have a dissolution profile in which at least 75% of the active ingredient is dissolved within 30 minutes, or at least 85% within 30 minutes, or at least 85% with 15 minutes, which is also dependent on the properties (e.g. intrinsic solubility) of the active ingredient Solid at room temperature means that the lower limit of the melting range of the triglyceride is higher than about 20° C. More preferably, the lower limit of the melting range of the triglyceride is higher than about 35° C. In other preferred embodiments, the melting range is from about 40° C. to about 85° C., or from about 45° C. to about 70° C. If more than one triglyceride is present in the coating, at least one of them representing a large fraction of the total triglyceride content in the coating should have a melting range according to one of these preferences. It is understood that the melting ranges are—as usually—given for a normal atmospheric pressure, e.g. approximately 1013 mbar.

In particular, native triglycerides often comprise fatty acid residues with different chain lengths and degrees of saturation, i.e. they represent mixtures of various chemically different triglycerides. For the sake of achieving more reproducible properties, triglycerides are therefore sometimes purified or semi-synthetically manufactured. Such more defined grades of triglycerides are also preferred according to the invention.

According to one of the preferred options, the triglyceride is a substantially pure triglyceride, having a chemical purity of at least about 90%, i.e. comprising only a small fraction of triglycerides with other fatty acid residues than the main fraction. In particular, the chemical purity of the triglyceride may be at least about 95%, or at least about 97%, respectively.

According to another one of the preferred options, the triglyceride is substantially saturated. In particular, the iodine value, which is a commonly used parameter to describe the degree of unsaturation in triglycerides and which reflects the mass of iodine in grams that is consumed by 100 grams of a triglyceride, may be lower than about 10, or not higher than about 5, or not higher than about 2, or not higher than about 1, respectively.

According to a further preferred option, the fatty acid residues of the triglyceride are substantially the same, i.e. at least about 80%, or at least about 90%, or even at least about 95% of the acyl chains have the same number of carbon atoms and degree of saturation. Particularly useful are saturated triglycerides having acyl residues of 10 to 30 carbon atoms. Also preferred are saturated triglycerides having acyl residues with a chain length of 14 to 22 carbon atoms. Especially preferred are coatings comprising a triglyceride which comprises at least one acyl chain having 16 to 18 carbon atoms.

Moreover, the triglyceride may be selected from trimyristin (also known as glyceryl trimyristate, mp ca. 56-57° C.), tripalmitin (also known as glyceryl tripalmitate, mp 61-65° C.), tristearin (also known as glyceryl tristearate, mp ca. 70-73° C.), triarachidin (also known as glyceryl triarachidate mp ca. 76-80° C.) and tribehenin (glyceryl tribehenate, mp ca 82-86° C.) respectively, especially from tripalmitin and tristearin. In a preferred embodiment, the triglyceride of the coating is selected from glyceryl tripalmitate and glyceryl tristearate. Optionally, two or more of these triglycerides may be used in combination.

Tripalmitin and tristearin, like many other saturated triglycerides, exhibit polymorphism. These triglycerides have an amorphous form and various crystalline forms, i.e. an unstable α-modification, a metastable β'-modification and a thermodynamically stable β-modification. Tripalmitin (in its stable β-form) typically has a melting range—as determined by DSC—of 61 to 65° C., whereas the melting range of tristearin is about 70 to 73° C.

Apart from the triglyceride, the coating comprises a surfactant. It has been surprisingly found by the inventors that coating compositions comprising certain surfactants in combination with a solid triglyceride, in particular non-ionic surfactants such as polysorbates, may be applied as hot-melt coatings at relatively low temperatures while leading to coated particles which do not undergo any major changes with respect to their drug release behaviour. Thus, the invention allows the coating of temperature-sensitive drugs while achieving a product with significantly improved physical stability.

This is in sharp contrast to the teachings of prior art according to which the use of triglycerides as hot-melt coating materials is discouraged because the polymorphism of the triglyceride leads to dissolution profiles changing over time. Without wishing to be bound by theory, the inventors currently believe that the surfactant content in the coating composition leads to an induction of the thermodynamically stable β-modification of the triglyceride at moderate temperatures, i.e. substantially below the recrystallisation temperature of the triglyceride, so that the β-modification is already formed at the time when the coating composition, applied to the core as a hot-melt, solidifies while cooling down, or shortly thereafter, i.e. within minutes or a few hours at the most. Without the surfactant content, the stable β-modification of tristearin, for example, would only be obtained at a temperature close to 60° C., and such temperature would be detrimental to thermolabile compounds.

In other cases, it may also be possible that the surfactant stabilises the α-form of the triglyceride. In both cases, the consequence is that no polymorph conversion takes place during storage, and thus no physical change to the coating with potential impact on the drug dissolution profile.

In one of the preferred embodiments, the coating comprises no further lipid or wax component other than the triglyceride described above. In particular, the coating may be free of higher melting components which require increased processing temperatures or which could lead to an obstruction of the spray nozzle, such as carnauba wax.

The surfactant in the coating is optionally a non-ionic surfactant. Examples of pharmaceutically acceptable non-ionic surfactants include, without limitation, polysorbates, mono- and diglycerides of fatty acids, propylene glycol esters, sucrose fatty acid esters, polyglycerol esters, sorbitan fatty acid esters, polyoxyethylene sorbitan fatty acid esters, polyoxyethylene fatty acid ethers and poloxamers. In particular, polysorbates, such as polysorbate 65, have been found very suitable in combination with tristearin and tripalmitin. Optionally, two or more surfactants may be used in combination.

The surfactant, in particular the non-ionic surfactant, according to one of the preferred options, has a hydrophilic-lipophilic balance (HLB) value in the mid-range, in particular from about 5 to about 15, as described by Griffin (Calculation of HLB Values of Non-Ionic Surfactants, Journal of the Society of Cosmetic Chemists 5 (4): 249-56, 1954). Also preferred is a non-ionic surfactant with an HLB value in the range from about 6 to about 14, or from about 7 to about 13, or from about 8 to about 12, respectively. For example, polysorbate 65 exhibits an HLB value of about 10.5, and polysorbate 85 has an HLB value of about 11.

Alternatively, the surfactant in the coating may also be an ionic surfactant, such as a phospholipid or sodium dodecyl sulfate. Optionally, two or more surfactants may be used in combination. Further optionally, two or more surfactants comprising at least one ionic surfactant and at least one non-ionic surfactant may be used in combination.

In order to achieve a pronounced stabilising effect on the triglyceride in the coating, it is recommended to incorporate the surfactant at a surfactant-to-triglyceride ratio of at least about 0.05. More preferably, the ratio is in the range from about 0.05 to about 0.5, such as about 0.1, 0.15, 0.2, 0.25, 0.3, 0.35, 0.4, or 0.45. The coating composition may comprise, or even essentially consist of, from about 50 to 95 wt.-% of triglyceride and from about 5 to 50 wt.-% surfactant, in particular from about 70 to 95 wt.-% of triglyceride and from about 5 to 30 wt.-% surfactant.

Preferably, the surfactant is dissolved in, or miscible with, the triglyceride in the molten state, i.e. the surfactant is not incorporated at level which results in the formation of an emulsion or suspension in the molten state in which the coating composition is applied to the core particle. In this way, there is little risk for the coating composition comprising the surfactant and triglyceride to separate into two phases at any time during or after the coating process, and a reduced risk for the clogging of nozzles during the coating process, as in the case of a suspension.

The coating may be free of other constituents, such that the coating essentially consists of triglyceride and a polysorbate surfactant. In fact, one of the preferred coating compositions essentially consists of about 70 wt.-% of tristearate and about 30 wt.-% of polysorbate 65. Another preferred coating composition essentially consists of about 90 wt.-% of tripalmitin and about 10 wt.-% of polysorbate 65. Applying one of these coating compositions, for example a coating composition comprising from 70 to 90 wt.-% triglyceride and from 10 to 30 wt.-% polysorbate to agglomerated active ingredient particles as a hot-melt is surprisingly effective in simultaneously achieving effective taste-masking as well as rapid drug release, without release profile changes during storage. This is particularly so with the active ingredient being ibuprofen, ibuprofen sodium or ibuprofen potassium. Alternatively, the coating may comprise one or more further excipients, such as one or more pore-forming agents, fillers, dyes or colouring agents, stabilisers, antioxidants, sweeteners, flavours, swelling agents, and the like.

Preferably, however, the triglyceride and the surfactant together represent at least about 50 wt.-% of the coating, and more preferably at least about 70 wt.-%, or at least about 80 wt.-%, 90 wt.-%, or 95 wt.-%, respectively. According to a further preferred option, any further excipients are only incorporated at a level in which they are dissolved in, or miscible with, the molten triglyceride when the coating composition is sprayed onto the core particle.

The thickness of the coating is selected with an eye on the size and shape of the core. For example, if core particles shaped as flakes or needles are to be taste-masked, this may require a larger relative amount of coating composition to be applied than in the case of substantially spherical core particles having the same surface area. It will be appreciated by the skilled person that different weight ratios of the coating to the core are required for different core sizes to obtain the same coating thickness.

For the coating of typical, somewhat irregularly shaped agglomerated active ingredient particles having a mass mean particle size, as determined by sieve analysis, in the range from about 100 to about 1000 μm, the amount of coating composition required to achieve taste-masking is at least about 20 wt.-%, and more preferably at least about 30 wt.-%, relative to the weight of the coated particles. For a more effective taste-masking, it may even be required to apply about 40 wt.-% relative to the weight of the coated particles of the coating composition or more, or about 50 wt.-% or more. On the other hand, the relative amount of coating composition should not be so high as to result in slow drug dissolution from the coated particles. The amount should therefore not be higher than about 75 wt.-%, such as about 70 wt.-% or less, or about 60 wt.-% or less, relative to the weight of the coated particles. Depending on the coating composition and the size and shape of the core particles, particularly useful ranges for the coating compositions may be from about 20 to 70 wt.-%, or from about 30 to 50 wt.-%, or from about 40 to 60 wt.-%, or from about 50 to 70 wt.-% relative to the total weight of the coated particle. This is particularly advantageous in the case of the active ingredient being ibuprofen, ibuprofen sodium or ibuprofen potassium.

In one of the particularly useful embodiments which simultaneously achieves effective taste-masking, rapid dissolution or immediate drug release, and a stable dissolution profile, core particles of agglomerated active ingredient such as ibuprofen or ibuprofen sodium or -potassium having a mass mean particle size of about 100 to about 1000 nm are coated with a coating essentially consisting of 70 wt.-% of tristearin and about 30 wt.-% of polysorbate 65, wherein the coating is applied as a hot-melt to the core particles at an amount of about 30 to 60 wt.-%, such as 50 wt.-%, relative to the weight of the coated particles. In another one of the particularly useful embodiments, the same core particles are coated with a coating essentially consisting of 90 wt.-% of tripalmitin and about 10 wt.-% of polysorbate 65, wherein the coating is applied as a hot-melt to the core particles at an amount of about 20 to 50 wt.-%, such as 30 wt.-%, relative to the weight of the coated particles.

The term 'essentially consisting' and related terms (e.g. 'consist' and 'consists') as used herein in reference to the coating means that no further components have been added to the coating, other than the named components in order to prepare the coating. Nevertheless, very small amounts of other materials may be present, such as impurities.

The coated particle according to the invention may be manufactured by various methods, including the coating of core particles by conventional solvent-based coating methods in which the coating composition is dissolved in an organic solvent and subsequently sprayed onto the core particles under conditions by which the solvent is evaporated.

More preferably, however, the coating composition is melted and sprayed as a hot-melt onto the core particles. In this manner, the use of an organic solvent and the associated negative environmental, health and safety hazards may be avoided. One of the aspects of the invention is a method for the preparation of the coated particle described above, comprising the steps of (a) providing a core particle comprising an agglomerated active ingredient, (b) providing a coating composition comprising a molten triglyceride and a surfactant, and (c) coating the core particle with the coating composition. In particular, the core contains at least about 10 wt.-% of active ingredient. In further preferred embodiments, the core comprises at least about 30 wt.-% of active ingredient, or at least about 50 wt.-%, or at least about 60 wt.-%, or at least about 70 wt.-%, or at least about 80 wt.-%, or at least about 90 wt.-%, or at least about 95 wt.-%, or even at least about 98 wt.-% of active ingredient, respectively. One of the preferred active ingredients in this context is ibuprofen, ibuprofen sodium or ibuprofen potassium.

In another preferred embodiment, the invention provides a method for the preparation of a coated particle comprising the steps of (a) providing a core particle comprising an agglomerated active ingredient, (b) providing a coating composition essentially consisting of a molten triglyceride and a polysorbate, and (c) coating the core particle with the coating composition, wherein the triglyceride is a material which is solid at room temperature (20-25° C.), and wherein the core particle has a sieve diameter in the range from about 100 nm to about 1,000 nm. Also in this embodiment, the same preferences with respect to the content of the active ingredient as described above apply.

The method may be carried out in any suitable coating equipment, whose precise configuration is selected in particular in consideration of the particle size of the core material. For example, the method may be performed in a fluid-bed coater or in an air flow bed coater.

One of the particular advantages of the invention is that the coating composition and process of the invention provides an effective means for the coating of the agglomerated active ingredient particles. Agglomerated particles of active ingredients typically have low mechanical stability and are not easily processed i.e. they cannot easily be coated as the mechanical, as well as thermal stress involved in most coating processes would lead to the diminution or disintegration of the agglomerate.

This typically results in substantially reduced coating efficiency, and also the generation of undesirable active ingredient dust. The active ingredient dust can hinder the coating equipment and coating process. The disintegration of the agglomerate during coating process can lead to unacceptable inconsistencies in active ingredient content of the coated particles. Moreover, in some instances, further agglomerates formed between the agglomerated active ingredient core and coating mixture may result, rather than a true layer of coating.

It has been found that the coating composition and method of the invention overcomes such issues. Efficient coating is achieved, and no agglomeration with the coating material is observed when the cores comprising an agglomerated active ingredient are sprayed with the coating composition comprising a triglyceride which is solid at room temperature and a surfactant. No substantial disintegration of the agglomerated active ingredient cores are observed. Importantly, the resulting coated particles are found to be effectively taste-masked and at the same time have fast dissolution profiles.

This is particularly true for compounds which are per se challenging to taste mask, such as ibuprofen sodium.

Another advantage of the invention is that the coating composition allows processing at rather low temperatures, thus being particularly suitable for the processing of drug substances which are sensitive to degradation at elevated temperatures. Generally, it is not very suitable to coat thermally labile active ingredients with hot-melt coating compositions requiring a high coating temperature, such as coating compositions based on carnauba wax or other waxes.

Preferably, the product temperature during the coating process is kept below about 60° C., in particular below about 55° C. According to a further preference, the product temperature is kept between about 20 and 50° C. while the coating composition is applied to the core particles as a melt. In this respect, the nature of the triglyceride in the coating should also be taken into account: In the case of a coating composition based on a lower melting triglyceride such as tripalmitin, the product temperature may be kept between about 20 and 35° C., whereas in the case of a coating composition based on a higher melting triglyceride such as tristearin, the product temperature may be kept between about 20 and 50° C., in particular between about 35 and 50° C., such as between about 40 and 48° C. Particularly preferred is the method for preparing a coated particle according to the invention which involves keeping the product temperature between 20 and 50° C. while performing step (c) of the method, and/or wherein step (c) is performed in a fluid-bed coater or air flow bed coater.

In a further aspect, the invention provides a pharmaceutical composition comprising the coated particle described above. The coated particles as disclosed herein a particularly suitable for being incorporated in a composition for oral administration, in particular in the form of granules, such as dispersible granules, effervescent granules, direct-to-mouth granules, or as a tablet, such as a dispersible tablet, an effervescent tablet, or an orally disintegrating tablet.

Particularly useful embodiments are oral formulations which consist of multiple units, or which disintegrate in the mouth of the patient into multiple units, such as direct-to-mouth granules or orally disintegrating tablet, because for these types of formulations the taste-masking effect of the multiple units is crucial for patient acceptability.

As used herein, direct-to-mouth granules are oral compositions designed for direct oral administration without water. Direct-to-mouth granules may represent mixtures of various types of multiple units, which units may be agglomerated and/or non-agglomerated particles. Often, such direct-to-mouth compositions represent mixtures of sweetening agents, such as sugars or sugar alcohols, flavours, and drug, any of which may be agglomerated or granulated.

An orally disintegrating tablet may be defined as solid single-unit dosage forms that rapidly disintegrates in the mouth of the patient without chewing, typically within less than about one or two minutes. Orally disintegrating tablets are usually pressed with lower compression forces than conventional tablets to obtain a higher porosity. Alternatively, their porosity may be increased by a drying or sublimation step for those tablets which contain a high amount of moisture or a sublimable excipient. With regard to their formulation, the optimised use of disintegrants, such as commonly used crosslinked polymers, low-substituted celluloses, or effervescent couples, further contribute to rapid disintegration. Popular is also the use a highly water soluble excipients which allow the actual dissolution of major parts of the formulations in the saliva, and which give a smoother mouthfeel compared to other formulations that disintegrate rapidly but leave mostly insoluble residues behind.

Further embodiments, options, and/or preferences are illustrated by the following examples.

EXAMPLES

Example 1: Hot-Melt Coating of Compacted Ibuprofen Sodium

Ibuprofen sodium dihydrate (66.5 wt. %) having a median particle size of 77.6 µm and Avicel PH 105 (33.5 wt. %) were roller-compacted (batch size 1000 g to 2000 g) using a roller compactor of type WP 120 Pharma (Alexanderwerk) at a roll speed of 3.5 rpm and screw feed speed of 80 rpm. The hydraulic pressure was 60 bar and sieves with mesh-sizes of 0.8 mm (Sample 1B) or 1.25 mm (Sample 1A) where used to form granules. The granules were then sieved (mesh-size 355 µm) to obtain granules having a sieve diameter above 355 µm.

The resulting granules (cores) were fluidised in a laboratory scale air flow bed coater (Ventilus V-1, Innojet Herbert Huettlin, Steinen, Germany) and maintained at a temperature of 28-30° C. A molten coating mixture of 90 wt.-% of tripalmitin (Dynasan 116) and 10 wt.-% of polysorbate 65 (Tween 65) was stirred at a temperature of 100° C. The molten coating composition was then sprayed onto the ibuprofen sodium dihydrate granules at a spray rate of 6.4-7.1 g/min with an atomising pressure of 0.8 bar until the desired amount of coating was achieved. It was confirmed by visual inspection that the core granules were not further agglomerated but coated with the coating composition. Samples of coated granules comprising 30-35 wt.-% of coating material (ref. Sample 1A and 1B) relative to their total weight were prepared in this manner.

Subsequently, the coated granules were tested with respect to their taste and dissolution behaviour. The dissolution test was carried in a paddle apparatus (USP). 400 mg of the coated granules were placed in dissolution vessels filled with 900 mL of dissolution buffer at pH 6.8 and stirred at 100 rpm at 37° C. The ibuprofen sodium dihydrate content was analysed by an established HPLC method (according to Ph. Eur.). Taste-masking was evaluated by a panel of experts using a subjective organoleptic taste test. Water (1 mL) was injected into the oral cavity of a participant before intake of a sample. An amount of coated particles equivalent to a 400-mg dose of ibuprofen sodium dihydrate was used for taste testing. The time prior to the participant's sensation of a soapy or unpleasant taste was recorded.

| Sample | Coating (wt.-%) | Drug Dissolution | Taste Test |
|---|---|---|---|
| 1A | 30 | 85% within 30 min | >50 s |
| 1B | 35 | 85% within 30 min | >50 s |

Example 2: Hot-Melt Coating of Compacted Paracetamol

Paracetamol (70 wt. %) and Avicel PH 105 (30 wt. %) were roller-compacted (batch size 1700 g; roller compactor: Alexanderwerk WP 120 Pharma) at a roll speed of 5 rpm, a screw feed speed of 35 rpm and a hydraulic pressure of 170 bar. A sieve with mesh-size of 1.25 mm was used to form the granules.

The resulting granules (cores) were fluidised in a laboratory scale air flow bed coater (Ventilus V-1, Innojet Herbert Huettlin, Steinen, Germany) and maintained at a temperature of 25-32° C. A molten coating mixture of 90 wt.-% of tripalmitin (Dynasan 116) and 10 wt.-% of polysorbate 65 (Tween 65) was stirred at a temperature of 100° C. The molten coating composition was then sprayed onto the paracetamol/acetaminophen granules at a spray rate of 8.1 g/min with an atomising pressure of 0.8 bar until an amount of 40 wt. % coating, relative to the total weight of coated granule, was achieved. It was confirmed by visual inspection that the core granules were not agglomerated but coated with the coating composition.

Subsequently, the coated granules were tested with respect to their taste and dissolution behaviour. The dissolution test was carried in a paddle apparatus (USP). 1000 mg of the coated granules were placed in dissolution vessels filled with 900 mL of 0.1 N HCl and stirred at 100 rpm at 37° C. The paracetamol content was analysed by an established HPLC method (according to Ph. Eur.). Taste-masking was evaluated by a panel of experts using a subjective organoleptic taste test. Water (1 mL) was injected into the oral cavity of a participant before intake of a sample. An amount of coated particles equivalent to a 400-mg dose of paracetamol was used for taste testing. The time prior to the participant's sensation of a bitter or unpleasant taste was recorded.

In result, it was found that the coated granules released 85% of the active ingredient within 30 minutes. The taste was found to be acceptable, as no bitter or unpleasant taste could be detected within 65 s, i.e. the coating provided effective taste masking.

Example 3: Hot-Melt Coating of Granulated Calcium Acetate

Calcium acetate granules (cores) were fluidised in a laboratory scale air flow bed coater (Ventilus V-1, Innojet Herbert Huettlin, Steinen, Germany) and maintained at a temperature of 25-32° C. A molten coating mixture of 90 wt.-% of tripalmitin (Dynasan 116) and 10 wt.-% of polysorbate 65 (Tween 65) was stirred at a temperature of 100° C. The molten coating composition was then sprayed onto the calcium acetate granules at a spray rate of 6.5 g/min with an atomising pressure of 0.8 bar until an amount of 30 wt.-% coating, relative to the total weight of coated granule, was achieved. It was confirmed by visual inspection that the core granules were not agglomerated but coated with the coating composition.

The coated granules were tested with respect to their dissolution behaviour. The dissolution test was carried in a paddle apparatus (USP). 100 mg of the coated granules were placed in dissolution vessels filled with 900 mL buffer at pH 1.2 and stirred at 50 rpm at 37° C. The calcium acetate content was analysed by an established AAS method. In result, 94% of the calcium acetate was released within 10 minutes.

Example 4: Hot-Melt Coating of Granulated Caffeine

Caffeine granules (cores) were fluidised in a laboratory scale air flow bed coater (Ventilus V-1, Innojet Herbert Huettlin, Steinen, Germany) and maintained at a temperature of 25-53° C. A molten coating mixture of 90 wt.-% of tripalmitin (Dynasan 116) and 10 wt.-% of polysorbate 65 (Tween 65) was stirred at a temperature of 100° C. The molten coating composition was then sprayed onto the caffeine granules at a spray rate of 6.5 g/min with an atomising pressure of 0.8 bar until an amount of 30 wt.-% coating, relative to the total weight of coated granule, was achieved. It was confirmed by visual inspection that the core granules were not agglomerated but coated with the coating composition.

The coated granules were tested with respect to their dissolution behaviour, directly after manufacture and during storage. The dissolution test was carried in a paddle apparatus (USP). 100 mg of the coated granules were placed in dissolution vessels filled with 500 mL of 0.1 N HCl and stirred at 100 rpm at 37° C. The caffeine content was analysed by an established HPLC method (according to Ph. Eur.).

| Storage | Dissolution |
|---|---|
| Initial | >80% within 20 min |
| 25° C./60% r.h. 3 months | >80% within 20 min |
| 40° C./75% r.h. 1 month | >80% within 20 min |
| 40° C./75% r.h. 3 months | >80% within 20 min |

Example 5: Hot-Melt Coating of Granulated Ibuprofen

Agglomerated ibuprofen DC 100 granules (cores) having a median particle size of 308 μm were fluidised in a laboratory scale air flow bed coater (Ventilus V-1, Innojet Herbert Huettlin, Steinen, Germany) and maintained at a temperature of 25-32° C. A molten coating mixture of 86 wt.-% of tripalmitin (Dynasan 116) and 14 wt.-% of polysorbate 65 (Tween 65) was stirred at a temperature of 100° C. The molten coating composition was then sprayed onto the ibuprofen granules at a spray rate of 6.4-7.1 g/min with an atomising pressure of 0.8-1 bar until 30 wt.-% of coating material relative to the total weight of the coated granules were obtained. It was confirmed by visual inspection that the core granules were not further agglomerated but coated with the coating composition.

Example 6: Preparation of Direct-to-Mouth Ibuprofen Granules

Direct-to-mouth granules were prepared by combining the coated granules of Example 5 with the following excipients:

| Component | mg/Dose |
|---|---|
| Example 5 coated ibuprofen (70 wt % ibuprofen) | 571.43 |
| Sorbitol | 548.57 |
| Xylitol | 290.00 |
| Citric acid | 12.00 |
| Monosodium citrate | 20.00 |
| Magnesium citrate | 30.00 |
| Sodium carboxymethylcellulose | 15.00 |
| Aspartame | 1.00 |
| Spearmint aroma | 1.50 |
| Cherry aroma | 8.50 |
| Magnesium stearate | 2.00 |

The invention claimed is:

1. An immediate release particle comprising a core and a coating, wherein the core consists of an agglomerated granule or pellet having a diameter in the range from about 100 μm to about 1000 μm, which core consists of an agglomerated active ingredient, and wherein the coating consists of a triglyceride which is solid at room temperature and a polysorbate surfactant.

2. The particle of claim 1, wherein the triglyceride comprises at least one acyl chain having 16 to 18 carbon atoms.

3. The particle of claim 1, wherein the surfactant is polysorbate 65 or polysorbate 85.

4. The particle of claim 3, wherein the polysorbate is polysorbate 65.

5. The particle of claim 1, wherein the coating comprises from 70 to 90 wt.-% triglyceride and from 10 to 30 wt.-% polysorbate.

6. The particle of claim 1, wherein the particle consists of the core and the coating.

7. The particle of claim 1, wherein the weight of the coating is from 20 to 70 wt.-% relative to the total weight of the coated particle.

8. The particle of claim 1, wherein the core has a diameter in the range from about 200 μm to about 500 μm.

9. The particle of claim 1, wherein the active ingredient is agglomerated ibuprofen or ibuprofen sodium salt.

10. The particle of claim 1, wherein the active ingredient comprises crystals of active ingredient.

11. The particle of claim 1, wherein the granule or pellet is prepared by wet or dry granulation.

12. The particle of claim 2, wherein the triglyceride is selected from tripalmitin and tristearin.

13. A pharmaceutical composition comprising the particle of claim 1.

14. The pharmaceutical composition of claim 13, wherein the composition is formulated as granules or as a tablet.

15. The pharmaceutical composition of claim 14, wherein the granules are dispersible granules, effervescent granules, or direct-to-mouth granules.

16. The pharmaceutical composition of claim 14, wherein the tablet is a dispersible tablet, an effervescent tablet, or an orally disintegrating tablet.

17. A method for the preparation of the particle of claim 1, comprising the steps of
   (a) providing a core particle consisting of an agglomerated active ingredient,
   (b) providing a coating composition consisting of a molten triglyceride which is a solid at room temperature and a polysorbate surfactant, and
   (c) coating the core particle with the coating composition.

18. The method of claim 17, wherein the product temperature is kept between about 20 and 50° C. while performing step (c), and/or wherein step (c) is performed in a fluid-bed coater or air flow bed coater.

19. A particle comprising a core and a coating, wherein the core consists of an agglomerated granule or pellet having a diameter in the range from about 100 μm to about 1000 μm, which consists of an agglomerated active ingredient, and wherein the coating consists of a triglyceride which is solid at room temperature and a polysorbate surfactant, said particle being obtainable by a method comprising the steps of
   (a) providing a core particle consisting of an agglomerated active ingredient,
   (b) providing a coating composition consisting of a molten triglyceride which is a solid at room temperature and a polysorbate surfactant, and
   (c) coating the core particle with the coating composition.

* * * * *